US009744374B1

(12) United States Patent
Bower, II et al.

(10) Patent No.: US 9,744,374 B1
(45) Date of Patent: Aug. 29, 2017

(54) THERAPEUTIC MAGNETIC DEVICE COMPRISING MAGNETITE [FE3 O4] FEATURING A MAGNETIC CIRCUIT

(71) Applicant: US-50 Holdings, LLC, Paonia, CO (US)

(72) Inventors: Jay W. S. Bower, II, Dunsmuir, CA (US); Michael L. Tennant, Paonia, CO (US)

( * ) Notice: Subject to any disclaimer, the term of this patent is extended or adjusted under 35 U.S.C. 154(b) by 532 days.

(21) Appl. No.: 14/140,020

(22) Filed: Dec. 24, 2013

Related U.S. Application Data

(60) Provisional application No. 61/748,072, filed on Dec. 31, 2012.

(51) Int. Cl.
*A61N 2/08* (2006.01)
*A61N 2/06* (2006.01)
*A44C 5/00* (2006.01)

(52) U.S. Cl.
CPC .............. *A61N 2/06* (2013.01); *A44C 5/0023* (2013.01)

(58) Field of Classification Search
CPC ........... A61N 2/00–2/12; A44C 5/0023; A61H 2201/10
USPC ......................................................... 600/15
See application file for complete search history.

(56) References Cited

U.S. PATENT DOCUMENTS

| | | | |
|---|---|---|---|
| 4,095,587 A | 6/1978 | Ishikawa | |
| 4,330,892 A * | 5/1982 | Fukushima | .......... A47C 31/003 5/421 |
| 5,344,384 A | 9/1994 | Ostrow et al. | |
| 5,642,739 A | 7/1997 | Fareed | |
| 5,707,333 A * | 1/1998 | Bakst | ....................... A61N 2/06 600/15 |
| 5,989,178 A | 11/1999 | Chiu | |
| 6,796,937 B1 | 9/2004 | Bates | |
| 2004/0126621 A1* | 7/2004 | Fukuda | ............... H01F 41/0273 428/692.1 |

(Continued)

OTHER PUBLICATIONS

Taniguchi N, Kanai S, Kawamoto M, Endo H, and Higashino H., 2004, "Study on Application of Static Magnetic Field for Adjuvant Arthritis Rat" Evidence Based Complementary and Alternative Medicine (eCAM) Sep. 1, 2004;1(2):187191. Kansai College of Oriental Medicine, Sennan-gun, Osaka, Japan. Source: PubMed/NCBI; http://www.ncbi.nlm.nih.gov/pmc/articles/PMC516457/.

(Continued)

*Primary Examiner* — Catherine B Kuhlman
(74) *Attorney, Agent, or Firm* — Shifrin Patent Law; Dan Shifrin

(57) ABSTRACT

A magnetic therapeutic device is provided, comprising a non-electrically conductive strand and a plurality of magnetic beads. Each bead has a hole through its center ("bead hole") and has a North pole edge and a South pole edge forming a magnetic field parallel to the bead hole. The plurality of beads are in a linear touching arrangement in which the North pole edge of a first bead touches the South pole edge of a second bead, the North pole edge of the second bead touches the South pole edge of a third bead, and continuing until the North pole edge of a next-to-last bead touches the South pole edge of a last bead and the North pole edge of the last bead touches the South pole edge of first bead, thereby completing a magnetic circuit.

5 Claims, 2 Drawing Sheets

(56) References Cited

U.S. PATENT DOCUMENTS

| | | |
|---|---|---|
| 2005/0148809 A1 | 7/2005 | Delaney |
| 2006/0111606 A1* | 5/2006 | Yee .......................... A61N 2/06 600/15 |
| 2008/0072622 A1* | 3/2008 | Brack ................. A44C 5/0023 63/3 |
| 2008/0184737 A1* | 8/2008 | Wiseman ............ A44C 11/002 63/3.1 |
| 2011/0054238 A1* | 3/2011 | Komatsu ................ A61N 2/06 600/15 |

OTHER PUBLICATIONS

Gmitrov, J., Ohkubo, C., Okano, H., 2002, "Effect of 0.25 T static magnetic field on microcirculation in rabbits" Bioelectromagnetics Apr. 2002; 23(3):2249. Source: PubMed/NCBI; http://www.ncbi.nlm.nih.gov/pubmed/11891752.

Kirschvink, J.L., Kobayashi, Kirschvink, A., and Woodford, B.J., 1992, "Magnetite biomineralization in the human brain" Proceedings of the National Academy of Sciences Aug. 15, 1992 89(16): 76837687 Source: NCBI/NLM/NIH; http://www.ncbi.nlm.nih.gov/pubmed/1502184.

"16"/40 cm Magnetic beads strands: Round"; http://magnetikbeads.com/mag_round.html.

"Magnetik Clasps"; http://magnetikbeads.com/mag_clasp.html.

"Nonconductive filament"; http://www.rapala.com/Superior/Superior,default,pd.html?start=1&q=sufix%20superior.

"Applied Magnetics Superstore"; Supermagnetstore.com.

* cited by examiner

THERAPEUTIC MAGNETIC DEVICE COMPRISING MAGNETITE [FE3 O4] FEATURING A MAGNETIC CIRCUIT

RELATED APPLICATION DATA

The present application is related to commonly-assigned and U.S. Application Ser. No. 61/748,072, filed on Dec. 31, 2012, and entitled THERAPEUTIC MAGNETIC DEVICE COMPRISING MAGNETITE [Fe3O4] FEATURING A MAGNETIC CIRCUIT, which application is incorporated herein by reference in its entirety.

TECHNICAL FIELD

The present invention relates generally to the field of therapeutic magnetic devices, such as those worn by humans and animals and, more particularly, to a therapeutic magnetic device and method of creating a therapeutic magnetic device having a magnetic field parallel to a plane of the device.

BACKGROUND ART

Although therapeutic magnetic devices in the form jewelry or other worn articles have been sold in the millions of units, there has been a frustrating lack of consistency or validation of results. Nevertheless, there is some evidence that magnets do influence microcirculation.

SUMMARY OF THE INVENTION

In one embodiment, the present invention provides a magnetic therapeutic device, comprising a non-electrically conductive strand and a plurality of magnetic beads. Each bead has a hole through its center ("bead hole") and has a North pole edge and a South pole edge forming a magnetic field parallel to the bead hole. The plurality of beads are in a linear touching arrangement in which the North pole edge of a first bead touches the South pole edge of a second bead, the North pole edge of the second bead touches the South pole edge of a third bead, and continuing until the North pole edge of a next-to-last bead touches the South pole edge of a last bead and the North pole edge of the last bead touches the South pole edge of first bead, thereby completing a magnetic circuit.

In another embodiment, the present invention provides a method of creating a magnetic therapeutic device, comprising providing a plurality of magnetic beads, each bead having a hole through its center ("bead hole") and having a North pole edge and a South pole edge forming a magnetic field perpendicular to the bead hole; the plurality of beads providing an axially polarized, ring-shaped permanent magnet having a central hole; passing the plurality of beads through the central hole of the permanent magnet near one edge of the permanent magnet, whereby the plurality of beads are coerced to orient their magnetic fields parallel to the axis of the bead hole, becoming realigned beads; and arranging the plurality of realigned beads in a linear touching arrangement in which the North pole edge of a first bead touches the South pole edge of a second bead, the North pole edge of the second bead touches the South pole edge of a third bead, and continuing until the North pole edge of a next-to-last bead touches the South pole edge of a last bead and the North pole edge of the last bead touches the South pole edge of first bead, thereby completing a magnetic circuit.

DETAILED DESCRIPTION OF THE PREFERRED EMBODIMENT

Figure 1:
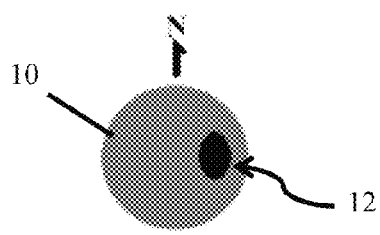
FIG. 1 illustrates a conventional, prior art 4 mm magnetite bead.

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Based on evidence from scientific research and their personal observations, the inventors are inclined to believe that the therapeutic magnetic device of the present invention may relieve pain and enhance circulation in a consistent manner. Many of the commercially available therapeutic magnetic devices in the form of jewelry or other worn articles rely on what may be referred to as "ejector technology" in which the placement of the axis of magnetic poles, and therefore the projection of a magnetic flux field through tissues, is perpendicular to the surface of the body.

In addition, many similar devices used in the field are composed of substances that feature strong magnetic properties but have no correlation in the human body. They may therefore be too powerful for the most efficacious result. Alternatively, even if the material used generates a magnetic circuit, it may not provide a significant subjective benefit.

It is well known in the field that there are electrical and magnetic currents within the body. The therapeutic magnetic device of the present invention may use magnetite ($Fe^3O^4$) beads to induce the magnetic field because biogenic ferromagnetic crystals, such as the naturally occurring magnetite that has already been found in brain tissues, interact more than a million times more strongly with external magnetic fields than do diamagnetic or paramagnetic materials (such as deoxy-hemoglobin, ferritin, and hemosiderin).

Experimentation based on the subjective responses of individual humans and the observable responses of animals (dogs and horses) led to the configuration and strength of field of the therapeutic magnetic device of the present invention described herein. Based on these observations, it is believed that the therapeutic magnetic device of the present invention, with its magnetic field substantially parallel to a surface of the body, has a consistent and beneficial influence on bodily functions in a manner markedly improved over conventional (flux field "ejector-based") examples.

It is believed that these results are due to special affinities that magnetically charged magnetite has with the mammalian organism and the configuration of the magnetic field in the form of a magnetic circuit around the length of the device; that is, parallel to a plane of the device rather than the aforementioned perpendicular (flux field "ejector") arrangement featured in most conventional therapeutic magnetic jewelry and appliances.

Figure 2:
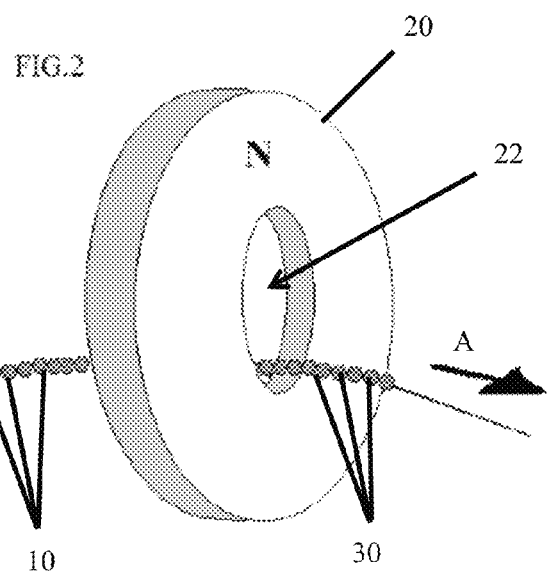
FIG. 2 illustrates an example of a method of coercing, or magnetic realignment, of beads utilizing a high strength magnetic field from axially polarized neodymium permanent magnet with the poles on the presenting and obscured surface.
Figure 3:
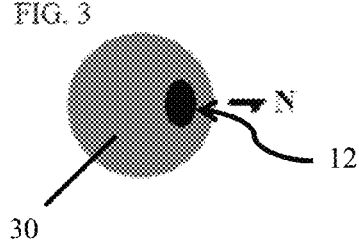
FIG. 3 illustrates the magnetically reoriented bead of FIG. 2 with the polarity aligned with the axis of the hole.

While magnetic beads 10 may be readily commercially available, they are typically hematite coated and in an undesirable polar alignment in which their magnetic fields are aligned perpendicular to the axis of the holes through their center ("bead hole"), indicated by the "N" (North) directional arrow in FIG. 1. Consequently, modification of the magnetic field of the beads is required. To do so, a very powerful, axially polarized, ring-shaped permanent magnet 20 (FIG. 2) may be used. Its North surface is indicated by the "N." A string of the beads 10 may be passed through a central hole 22 in the magnet 20, in close proximity and parallel to the greatest concentration of flux lines; that is, near one edge of the magnet. As the beads 10 pass through the magnet 20 in the direction indicated by the arrow "A," they are coerced to orient their magnetic fields parallel to the axis of the bead hole 12, becoming realigned beads 30. The new magnetic orientation is indicated in FIG. 3 by the "N" direction arrow. Coercion of the beads' magnetic fields may also be performed by an electromagnet of similar strength, during or after manufacture.

Better results may be provided by beads primarily comprising magnetite (typically naturally contaminated with small amounts of hematite). The device may have a field strength of between about 100 and about 2,000 gauss (about 10 mT to about 200 mT) measured at the greatest concentration of flux lines, the juncture of the poles between adjacent beads.

Figure 4:
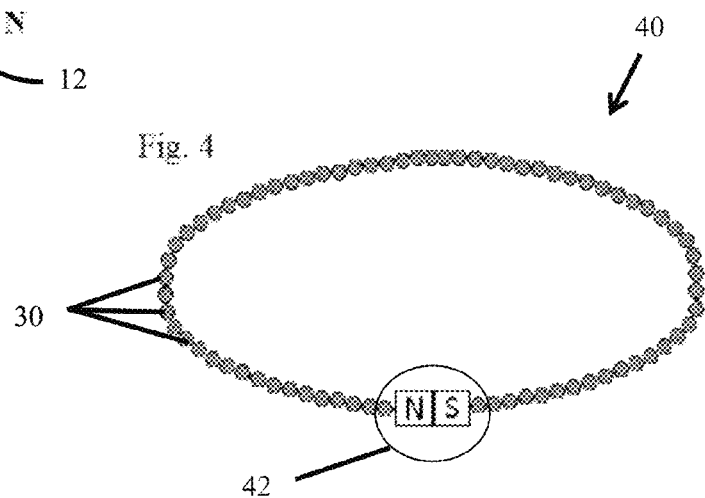
FIG. 4 illustrates an example of a therapeutic magnetic device of the present invention in the form of a bracelet or necklace incorporating the reoriented beads illustrated in FIG. 2.

The device may be configured in the form of a plurality of magnetic beads 30 with their magnetic poles aligned with the axis of the bead hole 12, arranged linearly with opposite poles touching, the "N" (North) edge of one bead to the "S" (South) edge of an adjacent bead, as illustrated in FIG. 4. Thus, a magnetic circuit may be created when beads at the two terminal ends are connected, "N" of one to "S" of the other, such as with a clasp 42.

Figure 5:
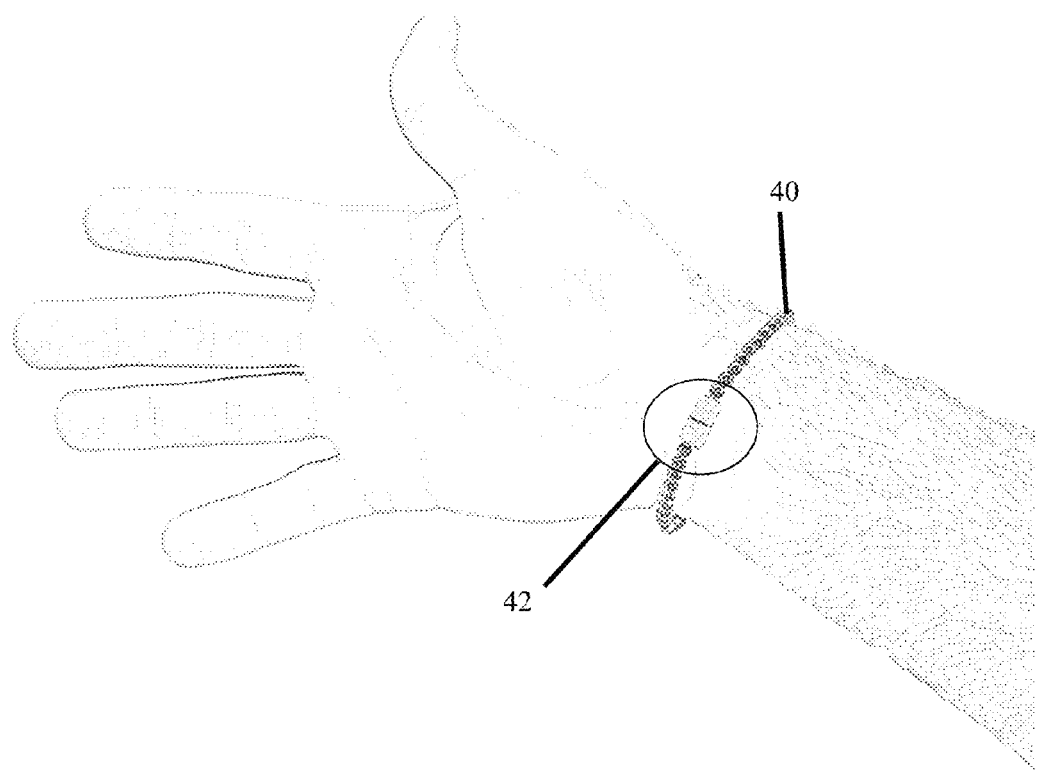
FIG. 5 illustrates the therapeutic magnetic device of FIG. 4 being worn as a bracelet by a user.

For ease of use as well as fashion, the therapeutic magnetic device may be configured as an article of jewelry to be worn around any central axis of the body or limbs of a human or animal, including the head, neck, arms, wrists, legs, ankles, or torso. For example, FIG. 4 illustrates an embodiment of the therapeutic magnetic device in the form of a bracelet or necklace 40 while FIG. 5 illustrates the device being worn as a bracelet 40 on a user's wrist. The beads 30 may be strung together on a non-electrically conductive strand of material 44 through their holes, such as high test monofilament or other high-tensile strength line approximately 0.8 mm in diameter (FIG. 2).

The clasp 42 may be nonmagnetic that allows the poles at each end of the device 40 to meet or may be magnetic. If a magnetic clasp is used, it may have a field strength of greater than about 4,000 gauss (400 mT) and be made of an aluminum-nickel-cobalt alloy (AlNiCo), a samarium-cobalt alloy (SmCo), or a neodymium-iron-boron alloy (NdFeB). The magnetic clasp 42 is interposed between the terminal (first and last) beads and oriented in the same manner as the beads. Its North and South pole ends will touch the adjacent beads' opposite pole ends, creating a contiguous or closed magnetic circuit ( . . . N, S, N, S, . . . ) of the device 40 (again referring to FIG. 4).

The preceding description presents only one form of the invention as contemplated by the inventors. A closed magnetic circuit made primarily of magnetite is used to illustrate the concept and not to limit the scope of the invention or limit it for human use. Various configurations may be made to suit the needs of individual humans or of animals such as pets (e.g. cats, dogs, etc.) or farm animals (e.g. horses, cows, pigs, etc.).

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A magnetic therapeutic device, comprising:
   a plurality of magnetic beads, each bead having a North pole edge and a South pole edge forming a magnetic field, each bead further having a hole through its center parallel to the magnetic field; and
   a non-electrically conductive strand threaded through the holes in the plurality of beads;
   the plurality of beads arranged linearly whereby the North pole edge of a first bead touches the South pole edge of a second bead, the North pole edge of the second bead touches the South pole edge of a third bead, and continuing until the North pole edge of a next-to-last bead touches the South pole edge of a last bead and the North pole edge of the last bead touches the South pole edge of the first bead, thereby completing a magnetic circuit having a field strength of between about 100 and about 2,000 gauss (about 10 mT to about 200 mT) measured at the juncture of the poles between adjacent beads.

2. The device of claim 1, wherein the magnetic beads comprise primarily of magnetite ($Fe^3O^4$).

3. A magnetic therapeutic device, comprising:
   a plurality of magnetic beads, each bead having a North pole edge and a South pole edge forming a magnetic field, each bead further having a hole through its center parallel to the magnetic field;
   a magnetic clasp interposed between a first bead and a last bead and having a North pole edge touching the South pole edge of the first bead and a South pole edge touching the North pole edge of the last bead; and
   a non-electrically conductive strand threaded through the holes in the plurality of beads and through the clasp, the plurality of beads and the clasp arranged linearly along the stand whereby the North pole edge of the first bead touches the South pole edge of a second bead, the North pole edge of the second bead touches the South pole edge of a third bead, and continuing until the North pole edge of a next-to-last bead touches the South pole edge of the last bead, thereby completing a magnetic circuit having a field strength of between about 100 and about 2,000 gauss (about 10 mT to about 200 mT) measured at the juncture of the poles between adjacent beads.

4. The device of claim 3, wherein the clasp is formed from a material selected from the group consisting of alloys of AlNiCo, SmCo, and NdFeB.

5. The device of claim 3, wherein the magnetic beads comprise primarily of magnetite ($Fe^3O^4$).

* * * * *